United States Patent
Bengi et al.

(10) Patent No.: US 10,010,285 B2
(45) Date of Patent: Jul. 3, 2018

(54) METHOD AND DEVICE FOR DETERMINING A DAMAGE CHARACTERISTIC VALUE OF A KIDNEY

(71) Applicant: SIEMENS AKTIENGESELLSCHAFT, München (DE)

(72) Inventors: Ali-Nejat Bengi, Erlangen (DE); Stefan Lautenschläger, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 507 days.

(21) Appl. No.: 14/432,204

(22) PCT Filed: Sep. 11, 2013

(86) PCT No.: PCT/EP2013/068828
§ 371 (c)(1),
(2) Date: Mar. 28, 2015

(87) PCT Pub. No.: WO2014/048754
PCT Pub. Date: Apr. 3, 2014

(65) Prior Publication Data
US 2015/0223744 A1 Aug. 13, 2015

(30) Foreign Application Priority Data
Sep. 28, 2012 (DE) ........................ 10 2012 217 724

(51) Int. Cl.
*A61B 5/00* (2006.01)
*A61B 5/20* (2006.01)
(Continued)

(52) U.S. Cl.
CPC .............. *A61B 5/201* (2013.01); *A61B 6/461* (2013.01); *A61B 6/481* (2013.01); *A61B 6/504* (2013.01);
(Continued)

(58) Field of Classification Search
CPC ......... A61B 5/201; A61B 6/481; A61B 6/504; A61B 6/5217; A61B 6/461
See application file for complete search history.

(56) References Cited

U.S. PATENT DOCUMENTS

| 2005/0215881 A1* | 9/2005 | Van Zijl | G01R 33/483 600/410 |
| 2008/0021306 A1* | 1/2008 | Van Zijl | A61B 5/055 600/419 |
| 2011/0098556 A1 | 4/2011 | Blomqvist et al. | |

FOREIGN PATENT DOCUMENTS

| CN | 101658428 A | 3/2010 |
| WO | WO2006131867 A1 | 12/2006 |

OTHER PUBLICATIONS

Chinese office Action for related Chinese Application No. 201380054993.4 dated Sep. 23, 2016 with English Translation.
(Continued)

*Primary Examiner* — Joel Lamprecht
(74) *Attorney, Agent, or Firm* — Lempia Summerfield Katz LLC (57) ABSTRACT

The invention relates to elements of a method (1) for determining a damage characteristic value of a kidney (2). Images comprising the kidney (2) and the kidney artery (3) are entered into the method (1), from a three-dimensional digital subtraction angiography which is carried out by administering a contrast medium at the proximal end of the kidney artery (3) and comprises a fill run and a mask run, said method (1) comprising the following method steps: S1) determining a parenchymal blood volume into which the subtractions from images of the fill run and the mask run of the three-dimensional digital subtraction angiography are entered, additionally determining an arterial input function and normalizing the parenchymal blood volume with said arterial input function; S2) segmenting the kidney (2),
(Continued)

determining an average normalized parenchymal blood volume value, and determining a total value of the parenchymal blood volume into which the normalized parenchymal blood volume values of the segmentation of the kidney (2) are entered; S3) receiving an average normalized parenchymal blood volume normal value and a total normal value for a parenchymal blood volume, and determining at least one damage characteristic value of the kidney (2) into which the average normalized parenchymal blood volume value and the average normalized parenchymal blood volume normal value and/or the total value of the parenchymal blood volume and the total normal value of a parenchymal blood volume are entered; S4) issuing the at least one damage characteristic value of the kidney (2).

11 Claims, 3 Drawing Sheets

(51) Int. Cl.
   *G06T 7/00*   (2017.01)
   *A61B 6/00*   (2006.01)
   *G06T 7/11*   (2017.01)
(52) U.S. Cl.
   CPC .......... *A61B 6/5217* (2013.01); *G06T 7/0016* (2013.01); *G06T 7/11* (2017.01); *G06T 2207/10072* (2013.01); *G06T 2207/30084* (2013.01); *G06T 2207/30104* (2013.01)

(56) References Cited

OTHER PUBLICATIONS

Tong, Han et al., "Evaluation of clinical application in diagnosis of brain tumor with dynamic contrast-enhanced perfusion MR imaging," Neurol. Neurosurg., vol. 6; No. 3, pp. 196-204 (2006).

Henry Krum: Ardian's Symplicity I: One Year Results Sympathetic Renal Denervation in Resistant Hypertension, in: Transcatheter Cardiovascular Therapeutics (TCT) Conference, Sep. 21-26, 2009, San Francisco, California, USA, 2009.

Michaely H.J. et al., "Functional renal imaging: nonvascular renal disease," Abdominal Imaging, Springer-Verlag, vol. 32, No. 1, pp. 1-16, ISSN: 1432-0509, DOI: 10.1007/s00261-005-8004-0, XP019514078, 2006, NE, Jan. 30, 2006.

Niamh Goulding: A new cure for hypertension—Renal Denervation, doctorate thesis, The Boolean, 2011, pp. 74-79 http://publish.ucc.ie/boolean/2011/00/Goulding/17/en, 2011.

Renal Denervation by RF Ablation in Patients with Refractory Hypertension, Dierk Scheinert, LINC Presentation, 2009.

Song T. et al., "Four Dimensional MR Image Analysis of Dynamic Renography," Proceedings of the 28th IEEE, EMBS Annual Inernatnal Conerence, New York, Aug. 30-Sep. 3, 2006, Engineering in Medicine and Biology Society, pp. 3134-3137, ISBN: 978-1-4244-0032-4, XP031339557, 2006, US, Aug. 30, 2006.

W.C. Cushman et al.: Success and Predictors of Blood Pressure Control in Diverse North American Settings: The Antihypertensive and Lipid-Lowering Treatment to Prevent Heart Attack Trial (ALLHAT), in: Journal of Clinical Hypertension (Greenwich), 2002, vol. IV, No. 6, pp. 393-404, 2002.

German Office Action for related German Application No. 10 2012 217 724.8, dated Jul. 18, 2013, with English Translation.

PCT International Search Report and Written Opinion of the International Searching Authority dated Nov. 25, 2013 for corresponding PCT/EP2013/068828.

\* cited by examiner

METHOD AND DEVICE FOR DETERMINING A DAMAGE CHARACTERISTIC VALUE OF A KIDNEY

This application is the National Stage of International Application No. PCT/EP2013/068828, filed Sep. 11, 2013, which claims the benefit of German Patent Application No. 10 2012 217 724.8, filed Sep. 28, 2012. The entire contents of these documents are hereby incorporated herein by reference.

BACKGROUND

The present embodiments relate to determining a damage characteristic value of a kidney.

Treatment-resistant hypertension describes a condition characterized by the inability to achieve a sufficient lowering of systolic blood pressure below 160 mmHg in spite of the, in some cases concurrent, administration of at least three antihypertensive agents, including diuretic. As indicated in W. C. Cushman et al., Journal of Clinical Hypertension, Vol. IV, No. VI, 2002, pp. 393 to 404, this disease affects even 8% of the optimally treated hypertensive patients, with an increasing trend; it therefore represents a very large patient cohort. The consequences of high blood pressure existing over many years may include: arteriosclerosis (atherosclerotic vascular disease); coronary heart disease (narrowing of the coronary blood vessels); myocardial infarction; cardiac insufficiency (chronic heart failure); atrial fibrillation; brain damage or stroke (high blood pressure being the primary risk factor for this); calcification or aneurysms of the aorta with risk of rupture and bleeding; kidney damage and renal failure; and/or eye damage with diminution of visual acuity.

Renal denervation, also known as renal sympathetic denervation, renal nerve ablation, renal denervation, or renal artery denervation, is a relatively new method for successfully lowering blood pressure in the long term. Denervation may be the complete or partial interruption of nerve tracts between an organ and the brain. Renal, from the Latin "ren", kidney, means "relating to the kidney" or "appertaining to the kidney". In renal denervation, an instrument known as an ablation catheter (e.g., a radiofrequency current ablation catheter) is typically introduced into the renal artery via an access site in the groin of a patient. A radiofrequency current is emitted, causing nerve fibers extending around the kidney vessel to be ablated, with the result that the corresponding nerve pathways, which in some instances conduct spurious signals from the kidney to the brain and back, are interrupted. The kidney is accordingly decoupled from the sympathetic nervous system.

By this method, it is possible, according to H. Krum, Transcatheter Cardiovascular Therapeutics (TCT) Conference, 2009, Sep. 21-26, 2009, San Francisco, Calif., USA, to achieve a clinically significant reduction in blood pressure of about 30 mmHg on average in approximately 80% of patients. Contrasting with the high success rate of 80%, there remain 20% of patients in whom no reduction in blood pressure may be achieved through renal denervation therapy. The cause for when the treatment works for a patient (e.g., the patient is what is called a "responder") and when it does not has not been conclusively explained to date. Currently, little to no attention is devoted to the difference between "responders" and "non-responders", attempts being made instead to treat as many patients as possible. This serves to help the medication-resistant patients, and a more extensive database is generated as a result. Current publications, such as in N. Goulding, A new cure for hypertension—Renal Denervation, The Boolean, 2011, put forward the hypothesis that the success of a renal denervation is dependent on the damage state of the kidney. Currently, this damage state of the kidney is measured by, for example, measuring the protein content in urine and/or blood. The creatinine level in the blood is also determined. However, these measurements only describe the state of damage of the kidney indirectly. Precise knowledge about the renal factors on which the regulation of blood pressure is dependent is so important because the kidney constitutes the primary medium- and long-term regulatory organ, with the short-term regulation being effected primarily by way of baroreceptors. The long-term regulation controls the blood pressure by sending signals via the nerves to the brain, resulting in a change in the total blood volume, the heart rate, and the change in vessel diameters. However, in certain circumstances, or under certain preconditions, the kidney also sends out "spurious" signals that lead to a pathological increase in blood pressure, without this being necessary for the body. The diseased kidney may also be the source of a pathological afferent signal that stimulates the efferent sympathetic activity. In the case of renal denervation, such signals from the kidney are prevented by the corresponding nerve tracks being ablated and thus deactivated. As a result the long-term regulation, which in the pathological case is incorrect, may be switched off, and the body regulates the blood pressure primarily by way of short-term regulation mechanisms, such as the baroreceptors.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method that enables a damage characteristic value of a kidney to be determined is provided. As another example, a device by which a damage characteristic value of a kidney may be determined is provided.

A method for determining a damage characteristic value of a kidney is provided. Images including the kidney and the renal artery obtained by a three-dimensional digital subtraction angiography scan carried out with administration of contrast agent at the proximal end of the renal artery and including a fill run and a mask run are input into the method. The method includes determining a parenchymal blood volume. The subtraction from images of the fill run and the mask run of the three-dimensional digital subtraction angiography scan is input into the parenchymal blood volume. An arterial input function is also determined, and the parenchymal blood volume is normalized by the arterial input function. The kidney is segmented, and an average normalized parenchymal blood volume value is determined. A total value of the parenchymal blood volume into which the normalized parenchymal blood volume values of the segmented kidney are input is determined. An average normalized parenchymal blood volume normal value and/or a total normal value of a parenchymal blood volume is received, and at least one damage characteristic value of the kidney into which the average normalized parenchymal blood volume value and the average normalized parenchymal blood volume normal value and/or the total value of the parenchymal blood volume and the total normal value of a parenchymal blood volume are input is determined. The at least one damage characteristic value of the kidney is output.

One or more of the present embodiments are based on the consideration that a renal denervation is medically successful, for example, when certain conditions that are responsible for the cited spurious signals are present. The method presented enables a damage characteristic value of a kidney that, based on perfusion properties and resistance characteristics of the arterioles, describes a decreased perfusion of the kidney to be determined. Perfusion or blood flow is the term generally used to describe the supply of organs or organ parts with blood. The blood for supplying tissues with oxygen and nutrients, for example, is supplied via arteries, while the outflow, for carrying away metabolic products and carbon dioxide, is effected via veins. A renal denervation treatment generally appears to be promising when the damage characteristic value of a kidney is comparatively large.

The medical examination of blood vessels (e.g., in angiography) is frequently undertaken by the digital subtraction angiography (DSA) method using digital, X-ray based imaging systems. In the method, at least one image (e.g., the mask or mask image) of a region that is to be examined (e.g., the kidneys) is acquired in the first instance in the background phase or mask phase by an X-ray machine. The image may also reveal bone structures, inter alia. Whereas in the further course of the examination, the uptake phase, arterial phase, subtraction phase, or fill phase, a contrast agent (e.g., an iodine-containing substance or an isotonic saline solution) is supplied to the vessels, further images (e.g., fill images) are acquired (e.g., after a delay of about 3 to 6 seconds, the reaching of what is termed the steady state, at relatively low frame repetition rates such as 0.5 to 6 frames per second). Thereafter, or at the same time, the mask image is subtracted in each case from the fill images by digital image processing. For example, the logarithmized grayscale values of the images are subtracted. What is obtained as result in the form of DSA result images are continuously anatomy-free images showing only the vascular system or the current location of the contrast agent. In addition to two-dimensional digital subtraction angiography acquisitions, three-dimensional digital subtraction angiography acquisitions, or 3D DSAs, are also known. In principle, these are obtained like 2D DSAs, with spatial images of the region that is to be examined being used. The spatial images may be obtained with the aid of a C-arm X-ray machine. According to the prior art, it is possible, by a suitable series of X-ray images acquired from different directions around the examination subject, to calculate a spatial image (e.g., a C-arm CT by analogy with computed tomography).

In one or more of the present embodiments, images obtained from a three-dimensional digital subtraction angiography scan performed in preparation for the method are accordingly input. The images include at least one kidney and an associated renal artery as the region to be examined. In this case, the three-dimensional digital subtraction angiography scan was performed with administration of contrast agent at the proximal end of the renal artery and includes a fill run and a mask run. Alternatively, the contrast agent injection may also have been administered in the aorta, proximally to the side branches of the renal arteries, and the three-dimensional digital subtraction angiography images include both kidneys and both associated renal arteries. This embodiment has the advantage that both kidneys are acquired for the method acts of the method according to one or more of the present embodiments.

In a first method act of the method, a parenchymal blood volume (PBV) is determined. Parenchyma, in medicine, may be a tissue (e.g., parenchymal tissue) that exercises a specific function and is in most cases enclosed by supporting connective tissue or carrier or structural tissue. In relation to the kidney, parenchyma denotes the tissue formed by the specific function cells of the kidney (e.g., the nephrons). The subtraction from images of the fill run and the mask run that were obtained in the three-dimensional digital subtraction angiography scan is input into the parenchymal blood volume. In one embodiment, the parenchymal blood volume is determined by the difference between the logarithmized grayscale values of the images from fill run and mask run:

PBV=fill run−mask run.

An arterial input function (AIF) is determined in addition. The arterial input function represents the average grayscale value, or average logarithmized grayscale value, of the renal artery or renal arteries. The parenchymal blood volume is normalized by the arterial input function. In one embodiment, the normalized parenchymal blood volume is visualized (e.g., in color-coded form) on a presentation device (e.g., a computer monitor). The normalization of the parenchymal blood volume with respect to the arterial input function (AIF) has the advantage that the representation and values of the normalized parenchymal blood volume are essentially independent of a contrast agent protocol (e.g., independent of injection site, density, dilution, flow rate, etc.), and consequently, is now essentially dependent only on the perfusion or on the blood volume of the kidney.

In a second method act of the method according to one or more of the present embodiment, the kidney or kidneys is/are segmented in the three-dimensional digital subtraction angiography images. Segmentation is a subsidiary discipline of digital image processing and of machine vision. Many segmentation methods (e.g., for generating regions related by content by combining neighboring pixels) in the spatial domain by combining neighboring voxels, according to a specific homogeneity criterion, are known in the technical literature. Pixel-, edge- and region-oriented methods are examples. Also known are model-based methods in which a specific shape of the objects is taken as the starting point, as well as texture-based methods in which an internal homogeneous structure of the objects may also be taken into account. An average normalized parenchymal blood volume value, henceforward denoted by $x_A$, is determined from the images of the segmented kidney or kidneys. A total value of the parenchymal blood volume of the kidney or kidneys, henceforward denoted by $x_B$, is determined in addition. The normalized parenchymal blood volume values of the segmented kidney or kidneys are incorporated into the determination of the total value of the parenchymal blood volume.

In a third method act of the method according to one or more of the present embodiments, an average normalized parenchymal blood volume normal value, henceforward denoted by $x_{A,Norm}$, and/or a total normal value of a parenchymal blood volume, henceforward denoted by $x_{B,Norm}$, is received. At least one damage characteristic value of the kidney is subsequently determined. The average normalized parenchymal blood volume value $x_A$ and the average normalized parenchymal blood volume normal value $x_{A,Norm}$ are input into a first damage characteristic value, henceforward denoted by $y_A$, and/or the total value of the parenchymal blood volume $x_B$ and the total normal value of a parenchymal blood volume $x_{B,Norm}$ are input into a second damage characteristic value, henceforward denoted by $y_B$.

In a fourth method act of the method according to one or more of the present embodiments, at least one damage characteristic value of the kidney, $y_A$ and/or $y_B$, is output.

The value(s) may be output, for example, as a numeric value or in color-coded form on a presentation means (e.g., a computer monitor).

An embodiment provides that a first damage characteristic value of a kidney is the percentage deviation of the average normalized parenchymal blood volume value from the average normalized parenchymal blood volume normal value, and/or a second damage characteristic value of a kidney is the percentage deviation of the total value of the parenchymal blood volume from the total normal value of a parenchymal blood volume.

This provides that in this embodiment the damage characteristic values, $y_A$ or $y_B$, which may also be interpreted as degrees of damage to the kidney, are calculated as percentage deviations of the normal values from the corresponding determined values, for example.

$$y_A = 1 - (x_A/x_{A,Norm}) \text{ or}$$

$$y_B = 1 - (x_B/x_{B,Norm}).$$

Another embodiment provides that a histogram of the parenchymal blood volume is incorporated into the determination of the arterial input function.

The arterial input function, which represents the average grayscale value or the average logarithmized grayscale value of the renal artery or renal arteries, is determined in this embodiment by a histogram analysis of the parenchymal blood volume.

In an embodiment, as an alternative to the determining of the arterial input function with the aid of a histogram analysis, the following method acts may be incorporated into the determination of the arterial input function:

receiving a segmented 3D dataset that includes the segmented kidney and the segmented renal artery; nonrigid 3D/3D registration of the parenchymal blood volume with the segmented 3D dataset; extracting the renal artery from the parenchymal blood volume; determining the arterial input function by averaging over the grayscale values of all pixels of the extracted renal artery of the parenchymal blood volume.

Since a segmentation of organs and vessels is often available as a function, for example, in modern medical imaging devices, such as computed tomography, magnetic resonance, or C-arm X-ray machines, it is possible in a first method substep to have recourse to an already segmented 3D dataset including the segmented kidney and the segmented renal artery. This is then received, for example, in a first method substep by the imaging device (e.g., transferred into a memory of a computing and control device).

In a second method substep, a nonrigid 3D/3D registration of the parenchymal blood volume with the segmented 3D dataset is carried out. Registration, image registration, or image fusion in digital image processing may be a process in which two or more images of the same or at least a similar scene are brought into the best possible correspondence with one another. During this process, one image may be defined as the reference image. The other images may be subject images. In order to achieve an optimal alignment of the subject images to the reference image, a compensating transformation is determined. The images to be registered may be different from one another if the images have been acquired from different positions, at different times, or by different imaging devices. Image registration methods are prevalent primarily in medical image processing, being used for bringing the images acquired by different imaging methods or modalities into alignment with one another. In such a process, a distinction may be made between rigid or inflexible registration methods and nonrigid or flexible registration methods. Registration by elastic models lends itself as a suitable method where there are complex local distortions between two images. In this case, the registration is generally accomplished iteratively through minimizing an energy functional. Registration algorithms for 3D images are digital image processing methods that are known per se.

In a third method substep, the renal artery is extracted from the parenchymal blood volume. Since the positions of the kidney and, for example, the renal artery are known from the segmented 3D dataset and these have been transferred into the parenchymal blood volume by the registration process, the renal artery may be extracted or determined from the parenchymal blood volume.

In a fourth method substep, the arterial input function is determined by averaging over the grayscale values of all pixels of the extracted renal artery of the parenchymal blood volume. A pixel may be a spatial picture element or voxel.

In a development of the last-described embodiment variant, the segmented 3D dataset received in the first method substep, which includes the segmented kidney and the segmented renal artery, and the nonrigid 3D/3D registration of the parenchymal blood volume with the segmented 3D dataset performed in the second method substep are incorporated with particular advantage into the segmentation of the kidney in the second method step. Since the positions of kidney and renal artery are known from the received segmented 3D dataset and these have been transferred into the parenchymal blood volume by the registration process, the kidney may be extracted or determined from the parenchymal blood volume. In other words, there are synergy effects that, for example, enable faster data processing to be leveraged.

In one embodiment, an addition of all of the normalized parenchymal blood volume values of the segmented kidney is input into the determination of the total value of the parenchymal blood volume.

In the second method act, the total value of the parenchymal blood volume is determined following segmentation of the kidney and determination of the average normalized parenchymal blood volume value. This is calculated by an addition of all of the normalized parenchymal blood volume values of the segmented kidney.

In one embodiment, the average normalized parenchymal blood volume normal value and/or the total normal value of a parenchymal blood volume are/is the average normalized parenchymal blood volume normal value and/or the total normal value of a parenchymal blood volume of a healthy examination subject.

As described, an average normalized parenchymal blood volume normal value $x_{A,Norm}$ and/or a total normal value of a parenchymal blood volume $x_{B,Norm}$ are/is received in the third method act and may be incorporated into the determination of the at least one damage characteristic value of the kidney. In one embodiment, the first damage characteristic value of a kidney is the percentage deviation of the average normalized parenchymal blood volume value $x_A$ from the average normalized parenchymal blood volume normal value $x_{A,Norm}$, and/or the second damage characteristic value of a kidney is the percentage deviation of the total value of the parenchymal blood volume $x_B$ from the total normal value of a parenchymal blood volume $x_{B,Norm}$. One or both normal values $x_{A,Norm}$ or $x_{B,Norm}$ may be corresponding values of healthy examination subjects (e.g., of healthy living creatures of the same species). The normal values may be derived, for example, from measurement series or statistics in which the corresponding values (e.g., the average normalized parenchymal blood volume value $x_A$ and/or the total value of the parenchymal blood volume $x_B$) have been determined for healthy examination subjects, such as human or animal patients.

In a further embodiment, the average normalized parenchymal blood volume normal value and/or the total normal value of a parenchymal blood volume are/is the average normalized parenchymal blood volume normal value and/or the total normal value of a parenchymal blood volume of an examination subject in the case of which a renal denervation treatment was not successful.

In this embodiment, the normal values are derived from examination subjects in the case of which a renal denervation treatment was not successful (e.g., from "non-responders"). This choice has the advantage that an increasing amount of statistical material would be available, which would increase the probability of a correct prediction.

In one embodiment, the normal values may be selected to correlate further characteristic values of the examination subject, such as sex, age, weight, type, and symptoms of the hypertension, with the current examination subject in order in this way to provide a better correspondence and comparison possibility.

In another embodiment, a warning is issued if the first and/or second damage characteristic value of a kidney lie/lies within a predefinable damage deviation range. The at least one damage characteristic value of the kidney is compared with a received damage deviation range, and a warning is issued, for example, in the form of a text output on a presentation device (e.g., a computer monitor) if the at least one damage characteristic value of the kidney lies within the damage deviation range. The damage deviation range is produced, for example, from a measurement series of a plurality of examination subjects that have been determined as "non-responders" (e.g., in the case of which a renal denervation treatment was not successful and whose damage characteristic values have been combined to form the damage deviation range). If a damage characteristic value of the kidney of a currently examined examination subject now lies within the damage deviation range, it is to be assumed that this examination subject also cannot be treated successfully by a renal denervation and a warning to this effect is issued. It is also conceivable that a probability value for a renal denervation treatment is indicated that is all the greater, the more the at least one damage characteristic value of the kidney deviates from the corresponding normal value of the kidney.

Further improvements may be achieved if the method is executed automatically.

Automatically executed methods require fewer interventions on the part of a user and as a result are generally less susceptible to error and are processed more rapidly.

In one or more of the present embodiments, a device for determining a damage characteristic value of a kidney is provided. The device includes a computing and control device having an input device and an output device. The computing and control device is configured to execute one of the above-described methods.

The computing and control device may be configured as a computer to which a monitor and a keyboard are connected as output device and input device, respectively. The capability enabling the method acts described in the features to be performed may include, for example, the loading, into the computing and control device, of a computer program that is executed for the purpose of carrying out the method acts.

The exemplary embodiments described in more detail hereinbelow represent variants of the present embodiments.

DETAILED DESCRIPTION

Figure 1:
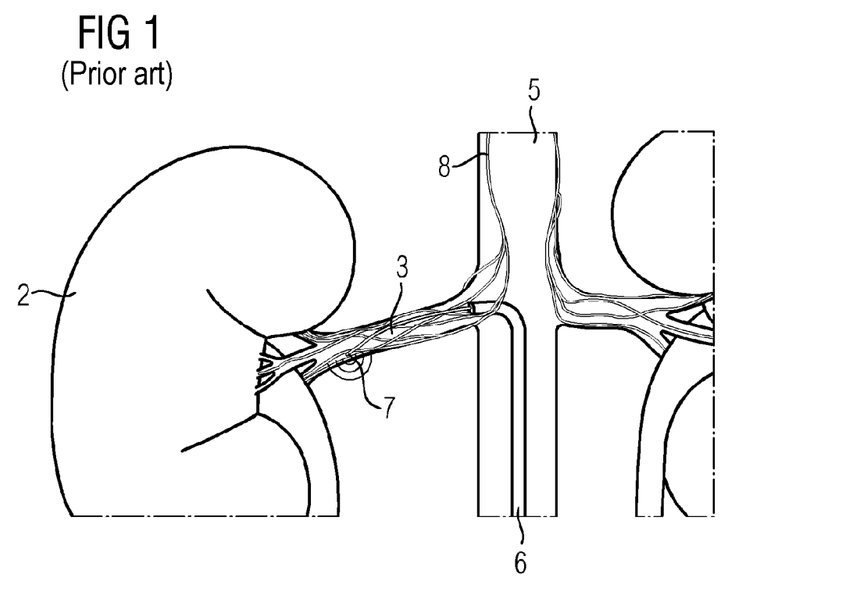
FIG. 1 schematically depicts a kidney in the case of which a renal denervation is performed.

FIG. 1 schematically depicts a kidney 2 in which a renal denervation is performed. Also shown in addition to the kidney 2 is an aorta 5 and a renal artery 3 connecting the aorta 5 with the kidney 2. Nerve fibers 8 extending around the renal vessel relay pathological stimulation signals, amongst others, to the brain. The signals are made responsible as causative of treatment-resistant hypertension. In renal denervation, an ablation catheter 6 is introduced into the renal artery 3, typically via an access site in the groin of a patient. A radiofrequency current, indicated by semicircles, is applied at a tip 7 of the ablation catheter 6, causing nerve fibers 8 extending locally around the renal vessel to be ablated. This results in the corresponding nerve pathways being electrically interrupted. The kidney 2 is accordingly decoupled from the sympathetic nervous system.

Figure 2:
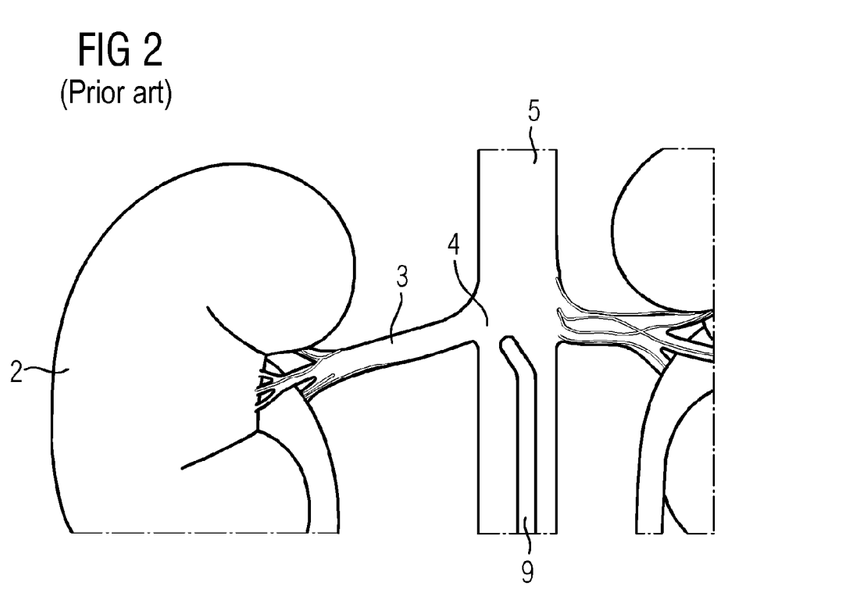
FIG. 2 schematically depicts a kidney prior to performing a digital subtraction angiography scan.

FIG. 2 schematically depicts a kidney 2 prior to a digital subtraction angiography scan being performed. In this method, at least one image (e.g., the mask or mask image) of, for example, the kidneys 2 and the renal artery 3 fed by the aorta 5 is acquired in the first instance in a background phase or mask phase by an X-ray machine. A catheter 9 is introduced via the aorta 5 as far as a point in front of the proximal end 4 of the renal artery 3 (e.g., the branch-off from the aorta 5). During the further course of the examination, in an uptake phase, arterial phase, subtraction phase or fill phase, a contrast agent (e.g., an iodine-containing substance or an isotonic saline solution) is supplied via the catheter 9 to the renal artery 3, and further images (e.g., fill images) are acquired, possibly after a delay of approximately 3 to 6 seconds, the reaching of the steady state. Once the fill run has terminated, the injection of the contrast agent may be stopped. The 3D images of the fill run and the mask run are input variables for a method according to one or more of the present embodiments for determining a damage characteristic value of a kidney. Digital subtraction of the mask images from the fill images results in 3D images or 3D volume images from which a parenchymal blood volume, for example, may be reconstructed.

Figure 3:
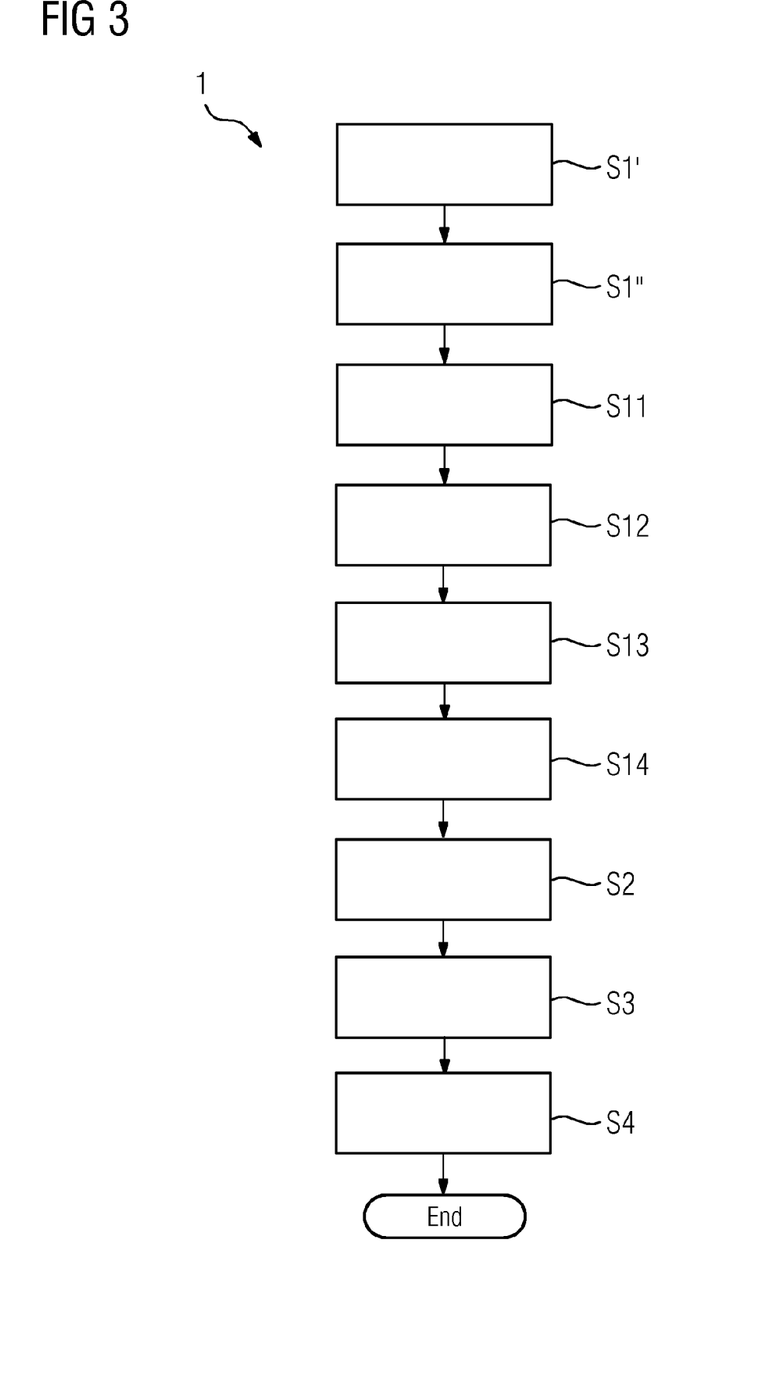
FIG. 3 is an exemplary flowchart of an embodiment of a method for determining a damage characteristic value of a kidney.

FIG. 3 shows, by way of example, a flowchart of an embodiment of a method 1 for determining a damage characteristic value of a kidney. The method 1 includes act S1', S1", S11 to S14, and S2 to S4. The method 1 starts with method act S1 and ends ("End") after method act S4. Images including the kidney and the renal artery that were acquired by a three-dimensional digital subtraction angiography scan performed with administration of contrast agent at the proximal end of the renal artery and includes a fill run and a mask run are input into the method 1. The method includes, in act S1', determining a parenchymal blood volume. The subtraction from images of the fill run and the mask run of the three-dimensional digital subtraction angiography scan is input into the parenchymal blood volume.

In act S1", an arterial input function is determined, and the parenchymal blood volume is normalized by the arterial input function. Method acts S11 to S14 are incorporated into the determination of the arterial input function. In act S11, a segmented 3D dataset that includes the segmented kidney and the segmented renal artery is received. In act S12, nonrigid 3D/3D registration of the parenchymal blood volume with the segmented 3D dataset is provided, and in act S13, the renal artery is extracted from the parenchymal blood volume. In act S14, the arterial input function is determined by averaging over the grayscale values of all pixels of the extracted renal artery of the parenchymal blood volume. In act S2, the kidney is segmented, and an average normalized parenchymal blood volume value is determined. A total value of the parenchymal blood volume into which the normalized parenchymal blood volume values of the segmented kidney are input is determined. In act S3, an average normalized parenchymal blood volume normal value and/or a total normal value of a parenchymal blood volume is received, and at least one damage characteristic value of the kidney, into which the average normalized parenchymal blood volume value and the average normalized parenchymal blood volume normal value and/or the total value of the parenchymal blood volume and the total normal value of a parenchymal blood volume are input, is determined. In act S4, the at least one damage characteristic value of the kidney is output.

Figure 4:
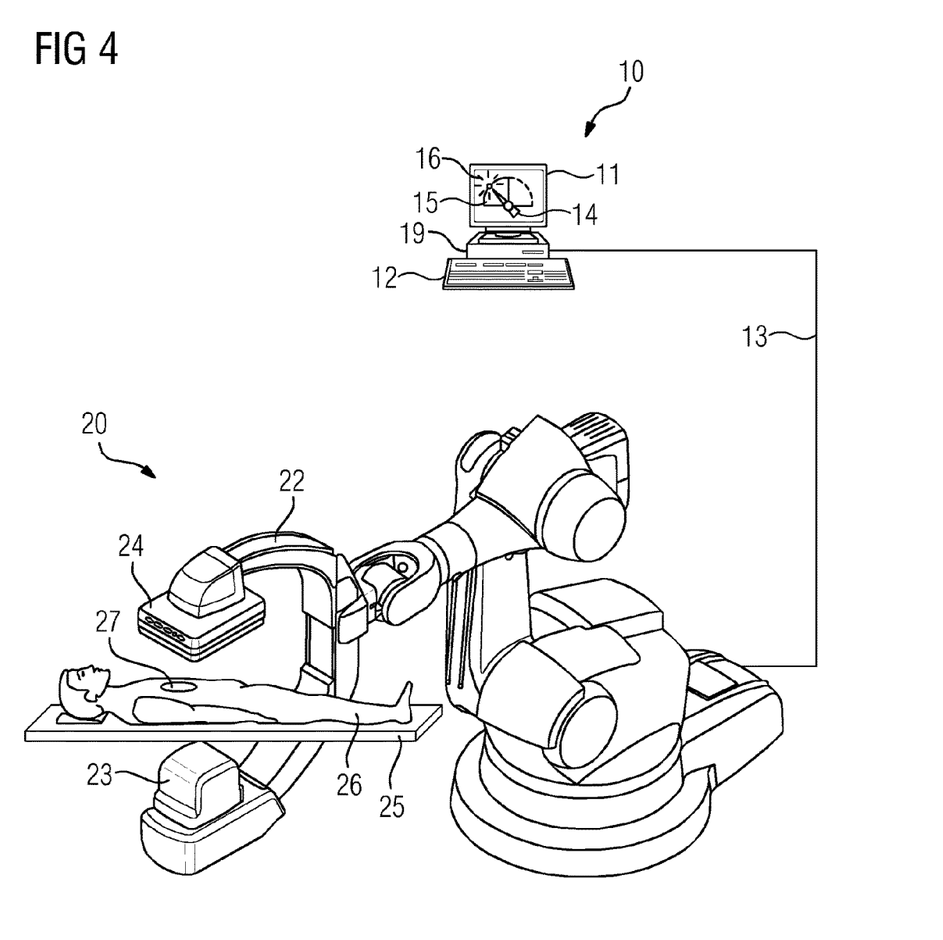
FIG. 4 schematically depicts an embodiment of a device for determining a damage characteristic value of a kidney.

FIG. 4 schematically depicts an exemplary embodiment of a device 10 for determining a damage characteristic value of a kidney. The device 10 includes a computing and control device 19 (e.g., a computer) having an input 12 (e.g., a computer keyboard) and an output 11 (e.g., a computer monitor). The computing and control devices 19 is configured to perform one of the described methods according to one or more of the present embodiments. For example, the computing and control device 19 is configured to receive images of a three-dimensional digital subtraction angiography scan that includes at least one kidney and one renal artery, the scan having been performed with administration of a contrast agent at the proximal end of the renal artery and including a fill run and a mask run. The device is coupled via a connector 13 (e.g., an electric cable) to an X-ray device 20. The X-ray device 20 has, for example, a C-arm 22 on which an X-ray source 23 and a digital X-ray detector 24 are arranged in opposite positions. An examination subject 26 (e.g., a human patient) lies on a support device 25 (e.g., an examination table) that is held by a pillar of the support device. The X-ray device 20 may be controlled by the computing and control device 19 (e.g., the computer). The C-arm 22 of the X-ray device 20 is rotatable. According to the prior art, a spatial image of an examination region 27 (e.g., the region containing kidneys and renal arteries of the examination subject 26) may be calculated based on a suitable series of X-ray images acquired from different directions around the examination subject 26 and may be transferred to the computing and control device 19. Inputs, such as the input of a damage deviation range 15, may be made on the input device 12 (e.g., the computer keyboard). A damage characteristic value of the kidney, represented, for example, as a deflection of a needle 14 in a vector diagram, may be visualized on the presentation device 21 (e.g., the computer monitor). Since the damage characteristic value, represented by the needle 14, lies within the damage deviation range 15, a warning 16 (e.g., represented symbolically by a flashing warning signal on the display device 11) is issued.

Further embodiments and advantages of the invention are described. The present embodiments provide a method that defines a value (e.g., a damage characteristic value of a kidney) that may help a user of the method (e.g., a physician) to estimate the chances of success of a renal denervation treatment. One or more of the present embodiments are based on the knowledge that a kidney having function values that lie within a "normal range" does not conduct any pathological signals to the brain and that the cause of a pathological increase in blood pressure does not lie with the long-term regulation by the kidney, but is determined by other factors. In this case, a renal denervation would not lead to medical success. In the case of a kidney having function values that lie outside of the "normal range", however, it is to be assumed that the heretofore described spurious signals do occur (e.g., that the pathological increase in blood pressure arises from spurious signals of the kidney). A renal denervation would be indicated in this case and may be performed. The probability that a renal denervation would be successful is to be estimated as significantly higher than in the first case.

The methodologies described offer the following advantages, amongst others: If one of the methods according to one or more of the present embodiments is performed frequently, the information base grows (e.g., as soon as medical studies have been conducted using one of these methods, physicians have a significantly higher degree of confidence as to whether a renal denervation is indicated, or whether this constitutes an unnecessary risk, such as renal artery stenoses for the patient); using one of the methods according to one or more of the present embodiments, it is reliably possible to submit for a renal denervation treatment only such patients that will also actually benefit from this form of therapy, and as a result, unnecessary, expensive treatments are avoided; the ability to implement the methods according to one or more of the present embodiments, together with imaging, decision making, and performance of the intervention, in the context of angiography, simplifies the logistics and the workflow in the hospital in comparison with known methods, the described methods according to one or more of the present embodiments are easy to handle for a user, because for the most part, the methods may be executed as automated procedures and as a result deliver only one or a small number of parameters having a significant content that is easy to interpret.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a damage characteristic value of a kidney, wherein images comprising the kidney and the renal artery obtained by a three-dimensional digital subtraction angiography scan carried out with administration of contrast agent at a proximal end of the renal artery and comprising a fill run and a mask run are inputs, the method comprising:

determining a parenchymal blood volume, wherein a subtraction from images of the fill run and the mask run of the three-dimensional digital subtraction angiography is input into the parenchymal blood volume, additionally determining an arterial input function and normalizing the parenchymal blood volume using the arterial input function;

segmenting the kidney, determining an average normalized parenchymal blood volume value, and determining a total value of the parenchymal blood volume into which the normalized parenchymal blood volume values of the segmented kidney are input;

receiving an average normalized parenchymal blood volume normal value, a total normal value of a parenchymal blood volume, or a combination thereof, and determining at least one damage characteristic value of the kidney into which the average normalized parenchymal blood volume value and the average normalized parenchymal blood volume normal value, the total value of the parenchymal blood volume and the total normal value of a parenchymal blood volume, or a combination thereof are input; and outputting the at least one damage characteristic value of the kidney.

2. The method of claim 1, wherein a first damage characteristic value of the at least one damage characteristic value of the kidney is a percentage deviation of the average normalized parenchymal blood volume value from the average normalized parenchymal blood volume normal value, a second damage characteristic value of the at least one damage characteristic value of the kidney is a percentage deviation of the total value of the parenchymal blood volume from the total normal value of a parenchymal blood volume, or a combination thereof.

3. The method of claim 1, wherein a histogram of the parenchymal blood volume is incorporated into the determination of the arterial input function.

4. The method of claim 1, wherein the determination of the arterial input function includes:

receiving a segmented 3D dataset that comprises the segmented kidney and the segmented renal artery;

nonrigid 3D/3D registering of the parenchymal blood volume with the segmented 3D dataset;

extracting the renal artery from the parenchymal blood volume; and determining the arterial input function, the determining of the arterial input function comprising averaging over grayscale values of all pixels of the extracted renal artery of the parenchymal blood volume.

5. The method of claim 4, wherein the received segmented 3D dataset, which comprises the segmented kidney and the segmented renal artery, and the nonrigid 3D/3D registration of the parenchymal blood volume with the segmented 3D dataset are incorporated into the segmentation of the kidney.

6. The method of claim 2, further comprising inputting an addition of all of the normalized parenchymal blood volume values of the segmented kidney into the determination of the total value of the parenchymal blood volume.

7. The method of claim 1, wherein the average normalized parenchymal blood volume normal value, the total normal value of a parenchymal blood volume, or a combination thereof is the average normalized parenchymal blood volume normal value, the total normal value of a parenchymal blood volume of a healthy examination subject, or a combination thereof.

8. The method of claim 1, wherein the average normalized parenchymal blood volume normal value, the total normal value of a parenchymal blood volume, or a combination thereof is the average normalized parenchymal blood volume normal value, the total normal value of a parenchymal blood volume of an examination subject in the case of which a renal denervation treatment was not successful, or a combination thereof.

9. The method of claim 2, further comprising issuing a warning when the first damage characteristic value, the second damage characteristic value, or the first damage characteristic value and the second damage characteristic value of the kidney lie within a predefinable damage deviation range.

10. The method of claim 1, wherein the method is executed automatically.

11. A device for determining a damage characteristic value of a kidney, wherein images comprising the kidney and a renal artery obtained by a three-dimensional digital subtraction angiography scan carried out with administration of contrast agent at a proximal end of the renal artery and comprising a fill run and a mask run are inputs, the device comprising:

a computing and control device comprising an input and an output, wherein the computing and control device is configured to:

determine a parenchymal blood volume, wherein a subtraction from images of the fill run and the mask run of the three-dimensional digital subtraction angiography is input into the parenchymal blood volume, additionally determining an arterial input function and normalizing the parenchymal blood volume using the arterial input function; and segment the kidney, determine an average normalized parenchymal blood volume value, and determine a total value of the parenchymal blood volume into which the normalized parenchymal blood volume values of the segmented kidney are input, wherein the input is configured to receive an average normalized parenchymal blood volume normal value, a total normal value of a parenchymal blood volume, or a combination thereof, and determine at least one damage characteristic value of the kidney into which the average normalized parenchymal blood volume value and the average normalized parenchymal blood volume normal value, the total value of the parenchymal blood volume and the total normal value of a parenchymal blood volume, or a combination thereof are input, and wherein the output is configured to output the at least one damage characteristic value of the kidney.

* * * * *